US00PP27736P3

(12) United States Plant Patent
Booman

(10) Patent No.: US PP27,736 P3
(45) Date of Patent: Feb. 28, 2017

(54) ***SARRACENIA* PLANT NAMED 'MEERKAT MOB'**

(50) Latin Name: ***Sarracenia* hybrid**
Varietal Denomination: Meerkat Mob

(71) Applicant: James Lawrence Booman, Vista, CA (US)

(72) Inventor: James Lawrence Booman, Vista, CA (US)

(73) Assignee: Zantedeschia Lynn Booman, Vista, CA (US)

( * ) Notice: Subject to any disclaimer, the term of this patent is extended or adjusted under 35 U.S.C. 154(b) by 127 days.

(21) Appl. No.: 14/544,491

(22) Filed: Jan. 13, 2015

(65) Prior Publication Data

US 2016/0205860 P1 Jul. 14, 2016

(51) Int. Cl.
*A01H 5/00* (2006.01)

(52) U.S. Cl.
USPC ..... Plt./477

(58) Field of Classification Search
USPC ..... Plt./477
See application file for complete search history.

*Primary Examiner* — Keith Robinson

(57) ABSTRACT

A new cultivar of *Sarracenia* plant named 'Meerkat Mob' that is characterized by long tubular shaped leaves with a vertical hood extending above the leaf opening, green leaves with red veins and a green peristome that is mottled dark pink on older leaves and a hood with sides that extend 15 to 20 mm. on each side of the leaf opening and lobes that extend downward 5 to 10 mm. below the leaf opening.

1 Drawing Sheet

Botanical classification: *Sarracenia* hybrid.
Variety denomination: 'MEERKAT MOB'.

BACKGROUND OF THE INVENTION

The present invention relates to a new and distinct cultivar of *Sarracenia* plant botanically known as *Sarracenia* hybrid and hereinafter referred to by the cultivar name 'Meerkat Mob'.

The new *Sarracenia* plant is the product of a breeding program conducted by the inventor in Vista, Calif. The objective of the breeding program is to create new ornamental carnivorous pitcher plants with large leaves, high leaf counts and distinctive leaf colors 'Meerkat Mob' originated from the crossing of a large number of unidentified proprietary selections of *Sarracenia* hybrid (not patented) in 2009. The exact parent plants are unknown. The resulting seeds were subsequently harvested and grown. 'Meerkat Mob' was selected as a single plant within the progeny of the stated cross in a controlled environment in Vista, Calif. in 2009.

Asexual reproduction of the new cultivar 'Meerkat Mob' first occurred by tissue culture in 2011 in Rancho Santa Fe, Calif. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Sarracenia* cultivar 'Meerkat Mob'. These traits in combination distinguish 'Meerkat Mob' as a new and distinct cultivar apart from other existing known varieties of *Sarracenia*.

1. *Sarracenia* 'Meerkat Mob' exhibits long tubular shaped leaves with a vertical hood extending above the leaf opening.

2. *Sarracenia* 'Meerkat Mob' exhibits green leaves with red veins and a green peristome that is mottled dark pink on older leaves.
3. *Sarracenia* 'Meerkat Mob' exhibits a hood with sides that extend 15 to 20 mm. on each side of the leaf opening and lobes that extend downward 5 to 10 mm. below the leaf opening.

'Meerkat Mob' can be compared to plants of an unidentified selection of *Sarracenia purpurea*. In side-by-side comparisons conducted by the inventor in Vista, Calif., plants of the new *Sarracenia* differed from plants of the unidentified selection of *Sarracenia purpurea* in the following characteristics:

1. *Sarracenia* 'Meerkat Mob' exhibits longer leaves than the leaves of the unidentified selection of *Sarracenia purpurea*.
2. *Sarracenia* 'Meerkat Mob' exhibits an inside hood surface that is covered with very small hyaline hairs. The unidentified selection of *Sarracenia purpurea* has an inside hood surface that is covered with prominent downward pointing hairs.
3. *Sarracenia* 'Meerkat Mob' exhibits leaf hood margins that are smooth and not wavy. The leaf hood margins of *Sarracenia purpurea* have undulations on each side of the hood.
4. *Sarracenia* 'Meerkat Mob' exhibits a hood with sides that extend on each side of the leaf opening. The sides have lobes that extend downward 5 to 10 mm. below the leaf opening. The unidentified selection of *Sarracenia purpurea* has longer lobes that extend downward 15 to 20 mm. below the leaf opening.

'Meerkat Mob' can be compared to plants of an unidentified selection of *Sarracenia leucophylla*. In side-by-side comparisons conducted by the inventor in Vista, Calif., plants of the new *Sarracenia* differed from plants of the unidentified selection of *Sarracenia leucophylla* in the following characteristics:

1. *Sarracenia* 'Meerkat Mob' exhibits a vertical leaf hood. The leaf hood of the unidentified selection of *Sarracenia leucophylla* curves over the leaf opening.
2. *Sarracenia* 'Meerkat Mob' exhibits leaves that radiate from the rhizome tip in a symmetrical spiral. The leaves of the unidentified selection of *Sarracenia leucophylla* radiate from the rhizome tip and side branches in a non-uniform pattern.
3. *Sarracenia* 'Meerkat Mob' exhibits a green leaf hood. The unidentified selection of *Sarracenia leucophylla* has white translucent chlorophyll free areas on the hood and the top of the leaf.
4. *Sarracenia* 'Meerkat Mob' exhibits leaf hood margins that are smooth and not wavy. The leaf hood margins of *Sarracenia leucophylla* are very wavy and undulating.
5. *Sarracenia* 'Meerkat Mob' exhibits hollow tube shaped leaves through the growing season. The leaves of the unidentified selection of *Sarracenia leucophylla* are flat in the spring developing into hollow tube shaped leaves in the summer.

*Sarracenia* 'Meerkat Mob' can be compared to *Sarracenia* 'Cobra Nest' (U.S. Plant Pat. No. 12,821). 'Meerkat Mob' is different than 'Cobra Nest' in the following characteristics:

1. 'Meerkat Mob' exhibits a smaller number of leaves than the number of leaves of 'Cobra Nest'.
2. 'Meerkat Mob' exhibits longer leaves than the leaves of 'Cobra Nest'. -

BRIEF DESCRIPTION OF THE DRAWING

The accompanying photograph illustrates the distinguishing traits of *Sarracenia* 'Meerkat Mob'. The plant in the photograph shows an overall view of a 24 month old plant.

The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Sarracenia* cultivar named 'Meerkat Mob'. Data was collected in Vista, Calif. from 24 month old plants grown in a polyethylene greenhouse in 10 cm. diameter containers. The time of year was autumn and the temperature range was 26-40 degrees Centigrade during the day and 18-22 degrees Centigrade at night. The light level was 3000 foot candles. No photoperiodic treatments were used. Color determinations are in accordance with The Royal Horticultural Society Colour Chart 2007 edition, except where general color terms of ordinary dictionary significance are used. The growing requirements are similar to the species. 'Meerkat Mob' has not been tested under all possible conditions and phenotypic differences may be observed with variations in environmental, climatic, and cultural conditions, however, without any variance in genotype.

Botanical classification: *Sarracenia* hybrid 'Meerkat Mob'.

Parentage: 'Meerkat Mob' originated from a cross of two unidentified proprietary selections of *Sarracenia* hybrid.

Propagation: Tissue culture.

Time to initiate roots on a tissue-culture plantlet: About 30 days at 20 degrees Centigrade.

Time to produce a rooted tissue-cultured plantlet: About 150 days at 20 degrees Centigrade.

Crop time: Approximately 18 months.

Temperature tolerance: 0 to 40 degrees Centigrade.

Annual or perennial: Perennial.

Root description: Central root with sparse side roots 1 mm. in diameter, 155C in color, maturing to 175D.

Plant shape: Upright carnivorous perennial plant with erect tubular leaves.

Plant growth habit: Compact; upright with strong leaves; leaves arise in a spiral from a rhizome tip; vigorous growth.

Containers: 10 cm. containers.

Plant height: Soil level to top of leaves 24 to 27 cm.

Plant width: 16 to 18 cm.

Foliage description:

*Leaf shape.*—Tubular to trumpet-shaped, smaller diameter at base and larger diameter at apex with peristome at opening; mostly erect to slightly leaning; keel on one side of leaf; large terminal hood; sessile.

*Hood shape.*—Hemispherical with wings on each side of opening and lobes that extend downwardly form each wing; apex rounded; margin entire.

*Number of leaves per plant.*—6 to 8.

*Leaf length.*—24 to 27 cm.

*Leaf diameter.*—4.1 cm. at apex and 8 mm. at base.

*Leaf texture (both surfaces).*—Glabrous.

*Keel length.*—18.5 cm.

*Keel width.*—1.7 cm.

*Hood dimensions.*—5.3 cm. in length and 7.7 cm. in width; sides of hood extend 15 to 20 mm. on each side of leaf opening; lobes extend downward 5 to 10 mm. below leaf opening.

*Hood texture.*—Outer surface glabrous; inner surface has fine hyaline hairs less than 0.5 mm. in length.

*Peristome dimensions.*—2.5 mm. in width at hood, 6 mm. in width at front.

*Peristome texture.*—Glabrous.

*Peristome color.*—144A; mature peristome mottled with 185B.

*Young leaf color outer surface.*—144B; hood color 144B.

*Young leaf color inner surface.*—144B; hood color 144B.

*Mature leaf color outer surface.*—144A; veins 185B; hood 144A with veins 185B.

*Mature leaf color inner surface.*—144A, upper 3 cm. mottled 185B; veins 185B, hood 144A with veins 185B.

Flower: 'Meerkat Mob' has not produced flowers to date.

Fruit and seed: 'Meerkat Mob' has not produced fruit or seed to date.

Disease and pest resistance: Plants of the new *Sarracenia* exhibit good resistance to fungal diseases including *Botrytis cinerea* and *Colletotrichum gloeosporioides*. Mature plants are susceptible to mealy bugs (*Myzus persicae*) on the rhizome. Young leaves susceptible to green peach aphids (*Pseudococcus longispinus*). Mature leaves not susceptible to green peach aphids.

The invention claimed is:

1. A new and distinct variety of *Sarracenia* plant named 'Meerkat Mob' as described and illustrated.

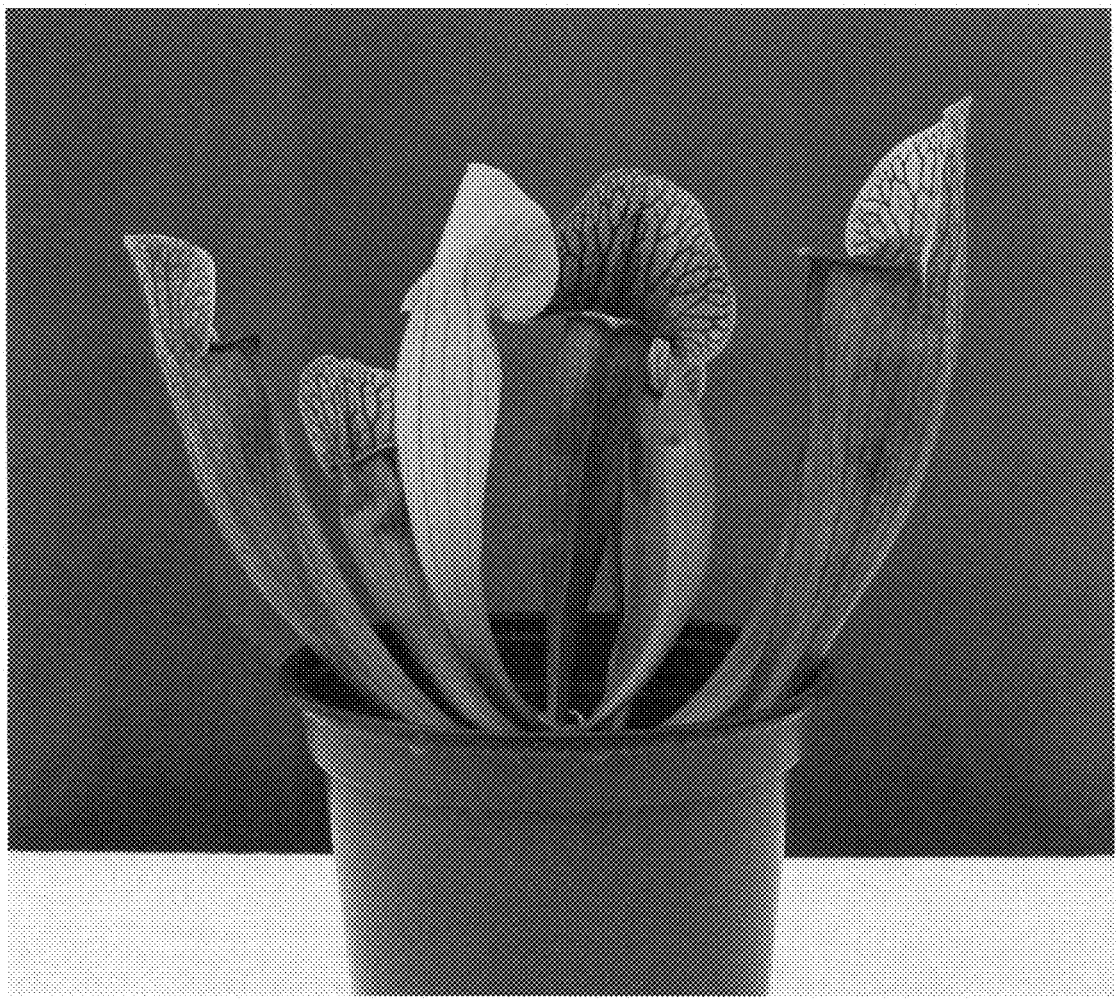

* * * * *